US011506801B2

United States Patent
Sauli et al.

(10) Patent No.: US 11,506,801 B2
(45) Date of Patent: Nov. 22, 2022

(54) PROMPT GAMMA MONITOR FOR HADRON THERAPY

(71) Applicant: EBAMED SA, Geneva (CH)

(72) Inventors: Fabio Sauli, Geneva (CH); Adriano Garonna, Geneva (CH)

(73) Assignee: EBAMED SA, Geneva (CH)

( * ) Notice: Subject to any disclaimer, the term of this patent is extended or adjusted under 35 U.S.C. 154(b) by 29 days.

(21) Appl. No.: 17/284,101

(22) PCT Filed: Oct. 10, 2019

(86) PCT No.: PCT/IB2019/058638
§ 371 (c)(1),
(2) Date: Apr. 9, 2021

(87) PCT Pub. No.: WO2020/075106
PCT Pub. Date: Apr. 16, 2020

(65) Prior Publication Data
US 2021/0286095 A1    Sep. 16, 2021

(30) Foreign Application Priority Data

Oct. 10, 2018 (WO) .................. PCT/IB2018/057833

(51) Int. Cl.
*H01L 27/146* (2006.01)
*G01T 1/29* (2006.01)
(Continued)

(52) U.S. Cl.
CPC .............. *G01T 1/29* (2013.01); *A61N 5/1048* (2013.01); *G01T 1/023* (2013.01); *G01T 1/20* (2013.01)

(58) Field of Classification Search
CPC .. G01T 1/29; G01T 1/023; G01T 1/20; A61N 5/1048
See application file for complete search history.

(56) References Cited

U.S. PATENT DOCUMENTS 3,399,302 A * 8/1968 Carrell ..................... G01T 1/20
250/390.04
2009/0206269 A1   8/2009 Kraft et al.
(Continued)

FOREIGN PATENT DOCUMENTS

| CN | 106291656 A | 1/2017 |
| DE | 102013102920 A1 | 9/2013 |

(Continued)

OTHER PUBLICATIONS

Perali et al., "Prompt gamma imaging of proton pencil beams at clinical dose rate", Physics in Medicine and Biology, vol. 59, pp. 25149-15-87 (Year: 2014).*

(Continued)

*Primary Examiner* — Kiho Kim
(74) *Attorney, Agent, or Firm* — Christensen, Fonder, Dardi & Herbert PLLC; Stuart J. Olstad

(57) ABSTRACT

A medical imaging tool is described, capable of providing in real time 2-D images of the prompt gamma fields released during patient treatment. Owing to its millimetre position accuracy, the instrument is particularly suited for applications where a precise determination of the end-of-range (Bragg peak) of the beam is of paramount importance, as in cancerous and non-cancerous targets for treatment with ion beams and for the treatment of atrial fibrillation. With its unique dual-layer conception in coincidence, the instrument has high rejection ability against false neutron-generated counts, the principal source of background noise for in-beam dose monitoring. It can also provide a coarse measurement of the gamma incidence angle, permitting a correction of the parallax error, main source of dispersion for large area detectors employing collimators.

17 Claims, 7 Drawing Sheets

Figure 1:
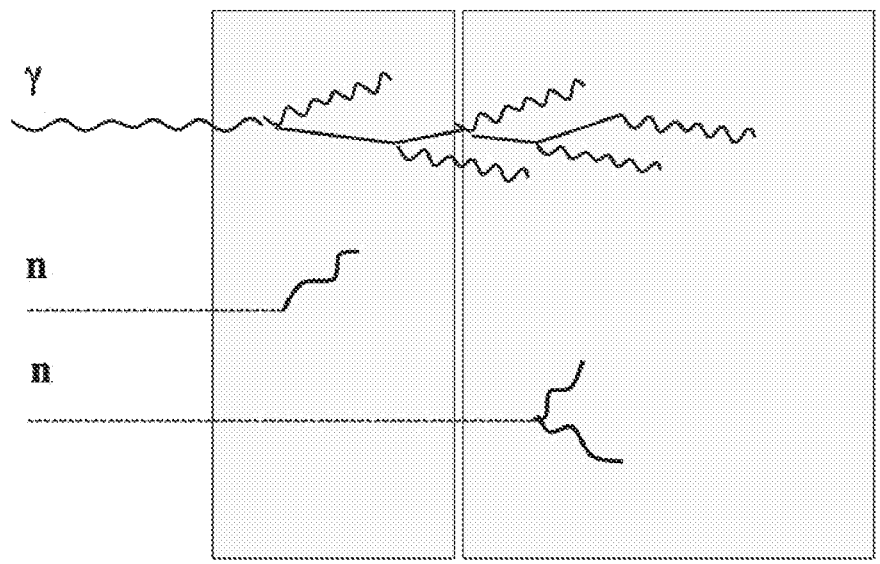

(51) Int. Cl.
*A61N 5/10* (2006.01)
*G01T 1/02* (2006.01)
*G01T 1/20* (2006.01)

(56) References Cited

U.S. PATENT DOCUMENTS

| | | |
|---|---|---|
| 2013/0053617 A1 | 2/2013 | Pu et al. |
| 2015/0331118 A1 | 11/2015 | Iltis |
| 2018/0252825 A1 | 9/2018 | Benlloch Baviera et al. |

FOREIGN PATENT DOCUMENTS

| | | | |
|---|---|---|---|
| DE | 102013112573 A1 | 6/2015 | |
| EP | 2140913 A1 | 1/2010 | |
| EP | 2290406 A2 | 3/2011 | |
| EP | 2 942 081 A1 | 11/2015 | |
| EP | 2950119 A1 | 12/2015 | |
| FR | 2930995 A1 | 11/2009 | |
| JP | 2006113061 A * | 4/2006 | ............ G01T 1/243 |
| JP | 2007047066 A | 2/2007 | |
| WO | WO 2009/111783 A2 | 9/2009 | |
| WO | WO 2011/012154 A1 | 2/2011 | |
| WO | WO 2012/104416 A1 | 8/2012 | |
| WO | WO 2012/152938 A2 | 11/2012 | |
| WO | WO 2015/025203 A1 | 2/2015 | |
| WO | WO2015/040225 A1 | 3/2015 | |
| WO | WO 2017/156113 | 9/2017 | |
| WO | WO 2020/075106 A2 | 4/2020 | |

OTHER PUBLICATIONS

Ortega PG et al: "Noise evaluation of Compton camera imaging for proton therapy" Institute of Physics and Engineering in Medicine, Physics in Medicine & Biology, vol. 60, No. 5, (Feb. 6, 2015), pp. 1845-1863.

Iguchi T et al: "Development of Compact Compton Gamma Camera for Non-Destructive Detection and Location of Hidden Explosives with Neutron Induced Prompt Gamma-Ray Imaging", 2005 IEEE Nuclear Science Symposium Conference Record, 2005 IEEE Wyndham El Conquistador Resort, Puerto Rico Oct. 23-29, 2005, Piscataway, NJ, USA,IEEE, vol. 2, (Oct. 23, 2005), pp. 735-739.

Braem et al. "AX-PET: A novel PET detector concept with full 3D reconstruction" Nuclear Instruments and Methods in Physics Research A 610 (2009) pp. 192-195.

Beltrame et al. "Construction and tests of demonstrator modules for a 3-D axial PET system for brain or small animal imaging" Nuclear Instruments and Methods in Physics Research A 636 (2011) pp. S226-S230.

Casella et al. "A high resolution TOF-PET concept with axial geometry and digital SiPM readout" Nuclear Instruments and Methods in Physics Research A 736 (2014) pp. 161-168.

Sauli, Fabio "Radiation Imaging with gaseous detectors" Nuclear Inst. and Methods in Physics Research, A 878 (2018) pp. 1-9.

Krimmer et al. "Prompt-gamma monitoring in hadrontherapy: A review" Nuclear Inst. and Methods in Physics Research, A 878 (2018) pp. 58-73.

Perali et al. "Prompt gamma imaging of proton pencil beams at clinical dose rate" Institut of Physics and Engineering in Medicine, Phys. Med. Biol. 59 (2014) pp. 5849-5871.

"Degiovanni, TERA, Novara, Italy and EPFL, Lausanne, Switzerland, Amaldi, et al., TERA, Novara, Italy Design of a Fast-Cycling High-Gradient Rotating Linac For Protontherapy" Proceedings of IPAC2013, Shanghai, China THPWA008, pp. 3642-3644.

Saint-Gobain Crystals Handbook, Scintillation Materials and Assemblies "About Saint-Gobain Crystals", Saint-Gobain Ceramics & Plastics Inc. 2004-2019.

Solevi, "Study of an in-beam PET system for CNAO, the National Centre for Oncological Hadrontherapy", PhD Thesis, Milano University, (2007) 144 pgs.

Watts "Detectors for Quality Assurance in Hadrontherapy" Doctoral Thesis, University of Barcelona (2013) 265 pgs.

* cited by examiner

PROMPT GAMMA MONITOR FOR HADRON THERAPY

RELATED APPLICATIONS

This patent application is a National Phase entry of PCT Application No. PCT/IB2019/058638, filed Oct. 10, 2019.

FIELD OF THE INVENTION

The present invention relates to the monitoring of prompt gamma rays that are generated during hadron therapies.

BACKGROUND

Radiation therapy with charged particles beams, also called ion beam therapy or hadron therapy, is a widely used method for the treatment of deep-seated tumors and other types of ailments in many hospital centers worldwide.

Since the beginning of hadron therapy, many approaches have been explored to monitor the dose distribution during a therapeutic session, recording and analyzing the distribution of the secondary radiation fields resultant from the beam-patient interactions: charged particles, neutrons, positron-emitting isotopes, gamma rays. Of all yields, the a-priori best candidate for imaging are prompt gamma rays, in the energy range between one and ten MeV, for several reasons:
- The emission intensity is proportional to the product of the local fluence of the slowing ions by the nuclear prompt gamma cross-section and in space uniquely correlates with the well-known Bragg peak.
- The emitted photons do not suffer the dispersive effect of multiple scattering on secondary charged particles and of time-dependent dilution for the positron emitters;
- The energy of the gammas, if measured, provides useful information on the constituents of the target;
- The prompt gamma field can be easily restricted by the use of collimators or pinhole camera systems, preserving the directionality information.

Gamma ray detectors are common instruments in particle and nuclear physics; they are however generally bulky and expensive due to the massive use of fast electronics used to record events. Moreover, they are often too sensitive to the intense neutron flux produced in the target and to the neutron field present in the irradiation room. There are also concerns on the radiation damage of sensitive electronics exposed to radiation.

An example of such a gamma prompt detector is disclosed in German patent application DE 102 2013 102 920 A1.

Recently, interest has been raised by the possibility of treating atrial fibrillation, a common risk factor for heart seizures (Amaldi 2013), and other cardiac arrhythmias. Even more than for standard neoplasm treatments, this modality requires a precise knowledge of the beam position, distribution and penetration depth in the patient, and is complicated by the blurring due to the patient's breathing motion and heartbeats. As already mentioned, the background counts due to the heavy yield of neutrons generated in the beam-patient interactions overlap with the prompt gammas signals.

A substantial improvement in the image quality has been obtained in previous works with a measurement of the time interval between the beam pulse and the detected signals; or time of flight (Perali 2014). This can only be implemented if the time of the beam pulse is known either by direct measurement or using the information provided by the accelerator, thus imposing strict limits to the rate and bunch structure of the beam.

GENERAL DESCRIPTION OF THE INVENTION

The present invention concerns an improved imaging instrument capable of recording continuously the position and dose of the irradiation imparted to a patient during a session of hadron therapy, thus permitting real-time interactive corrections to the treatment plan.

The invention more precisely concerns a prompt gamma monitor for patient dose monitoring in hadron therapy, said monitor comprising a first and second contiguous and independent detection modules that are configured in a way as to let prompt gammas coining from a patient initially interact with the first module and generate an electromagnetic shower propagating to the second module, wherein the first module is thick enough to collect sufficient signal from the incoming neutron or photon, but thin enough to enable the electromagnetic shower from the photon interaction to propagate to the second module and to limit the natural lateral spread of the electromagnetic shower and wherein the second module is thick enough to absorb practically all the energy from the said electromagnetic shower, said monitor furthermore comprising a signal detecting unit that is adapted to detect an electronic signal coincidence between the two detection modules.

Preferably, the thickness of the first module is typically between 5 mm and 100 mm.

Preferably, the thickness of the second module is typically between 5 and 100 mm.

The dual-layer concept, i.e. the contiguous two detection modules, results in an effective suppression of the false counts induced by the field of neutrons copiously generated during the patients' exposures. For large area devices using pinhole or knife edge collimators, analysis of the detected signals distributions in the two layers provide a coarse information on the angle of incidence of the primary gamma ray and permits to grossly correct for the often present parallax error thus improving the resolution in the measurement of the end-of range falloff.

The present invention is, in comparison with existing systems, compact and light. It provides images of the radiation fields in real time, allowing on-line correction of motion artifacts. The monitor according to the invention uses an electronic signal coincidence between the two detection modules, to differentiate hard photons, showering through the system, distinct from the background neutron interactions that remain localized in the first or second detection module and can be subtracted from the recorded images. In addition to the signal coincidence, one of the following additional features may further improve the signal to noise ratio:
- Introduction of a neutron absorber to reduce the flux of incoming neutrons,
- Filtering of the coincidence signals based on the collected energy in a suitable range, where prompt-gammas have a peak in distribution contrary to neutrons, which have rather constant spectrum,
- Filtering of the coincidence signals based on the angular correlation between the two layers, i.e. by selecting only the signals where there is a small position difference between the signal in the two layers, since gammas rays are generating signals only in a cone of angles from the Bragg peak to the detector whereas neutron interactions generate signals in any direction between the first and the second layers.

Those features may also be combined and used simultaneously.

DETAILED DESCRIPTION OF THE INVENTION

The invention will be better understood hereafter, with some non-limiting examples and with the following figures:

FIG. 1: Operating principle of the dual-layer Prompt Gamma Monitor (PG-MON) according to the invention, with two contiguous and independent detection modules. Prompt gammas from the beam-target interactions interact in the first module and generate an electromagnetic shower propagating to the second module until full absorption, (The number of gammas in a shower is exaggerated for illustration purposes). The prongs due to neutrons interactions remain instead confined in only one of the two modules.

Figure 2:
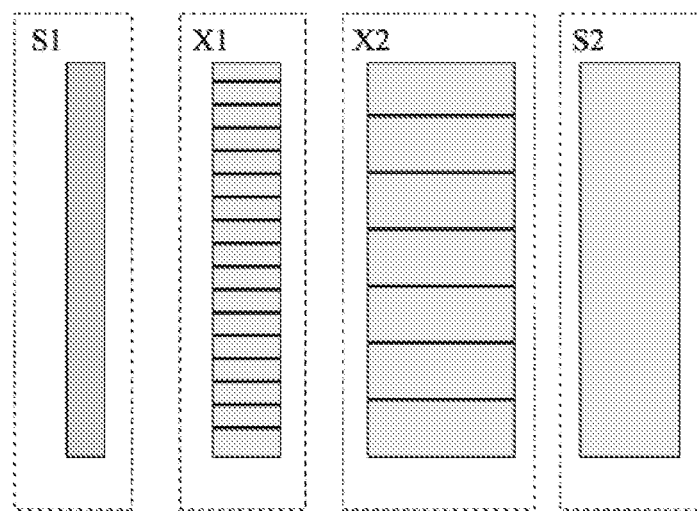

FIG. 2: Block schematics of the PG-MON (elements not to scale). X1 and X2 are independent scintillating crystals assemblies; S1 and S2 are light sensors used to detect and localize the scintillation photons. In one of the preferred embodiments, sensors arrays are mounted on both sides of each crystal assembly.

Figure 3:
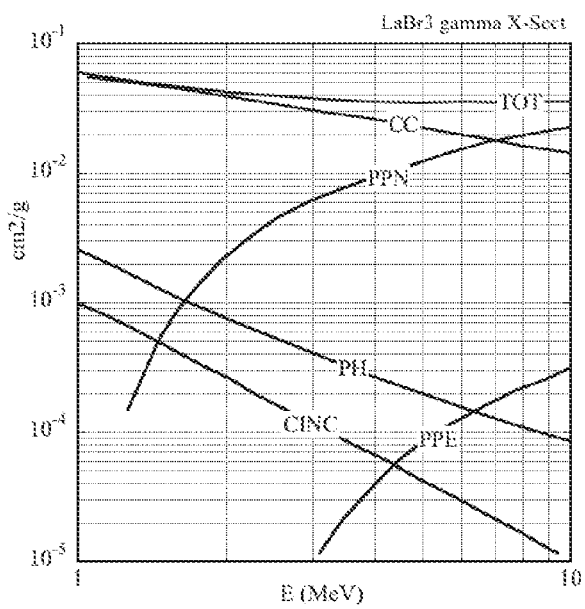

FIG. 3: Mass absorption coefficient of lanthanum bromide crystals for photons between 1 and 10 MeV. TOT: total, CC: Compton coherent; PPN: pair production in nuclear field; PH: photoelectric; CINC: Compton incoherent; PPE: pair production in electron field.

Figure 4:
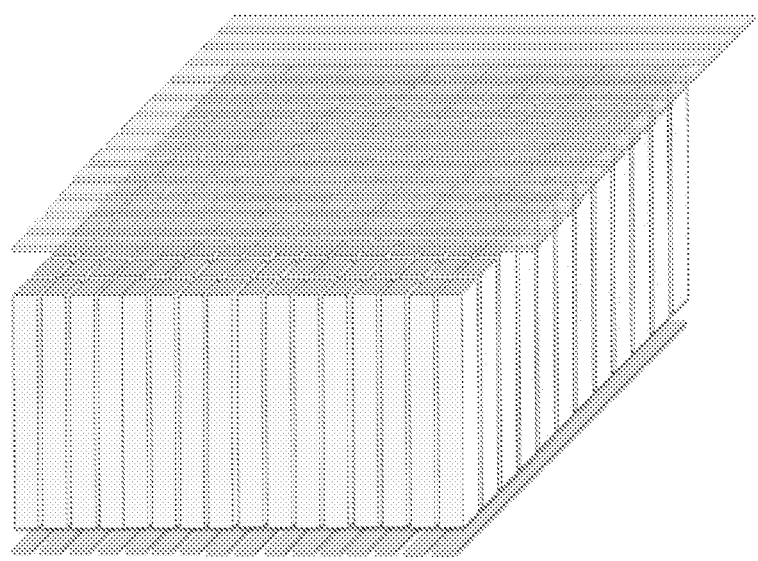

FIG. 4: Schematics of one possible embodiment of the projective readout system. Sets of perpendicular WLS bars collect the light from both edges of the scintillator rods and transmit it to a linear array of SiPM sensors at one end of the sets.

Figure 5:
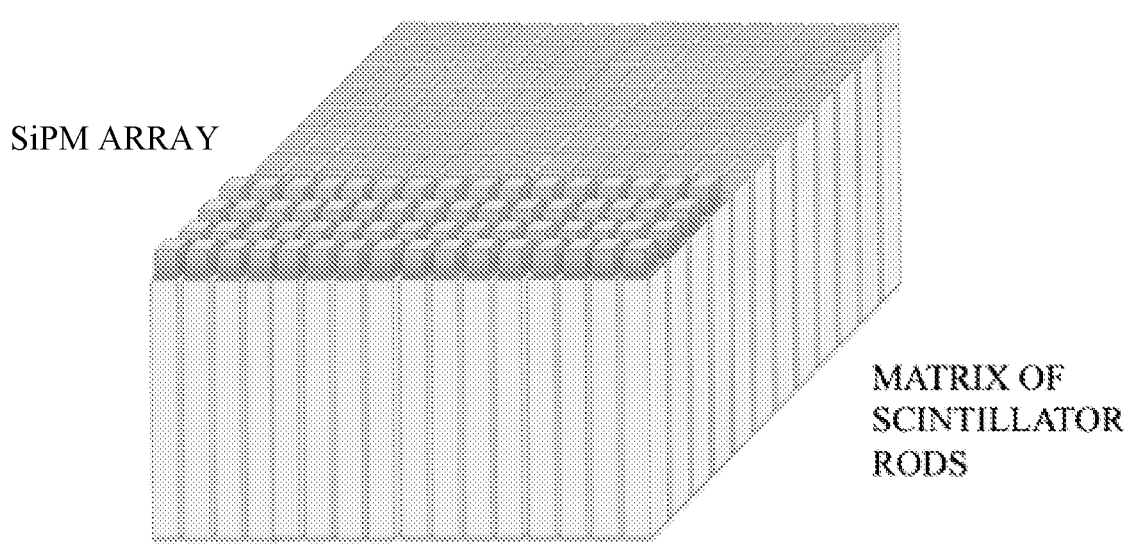

FIG. 5: Example of matrix of scintillator rods and reading mechanism with matrix of SiPM, as opposed to the WLS bars.

Figure 6:
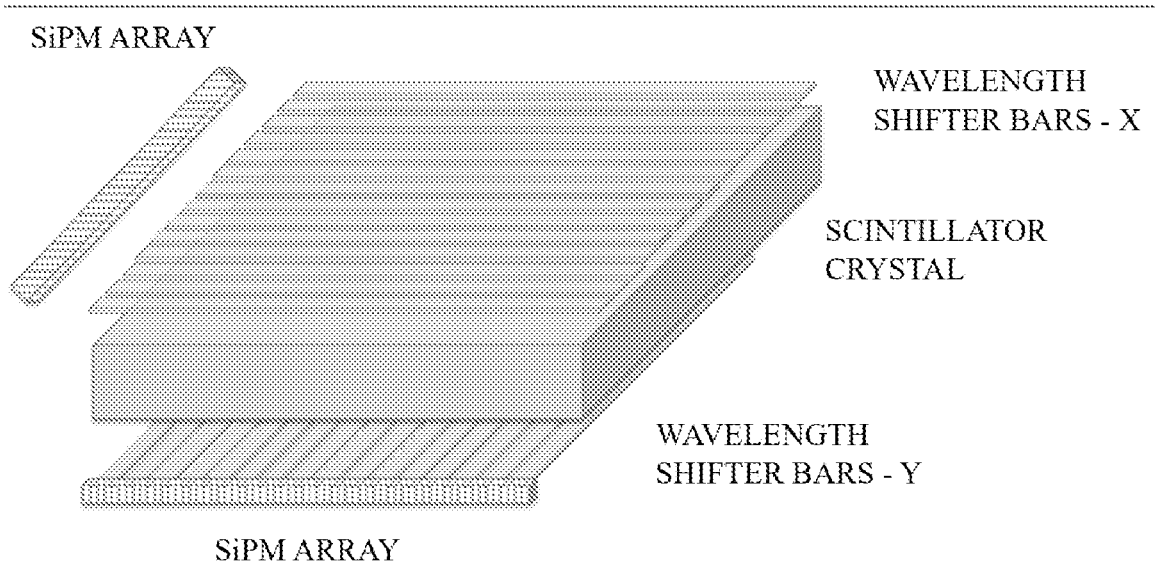

FIG. 6: Example of monolithic crystal arrangement where the signal collected on the WLS strips can be fitted to determine the hit position, without the need to have pixelized crystals. The analysis of the signals collected on the two sets of strips gives information on the depth of interaction, allowing the correction of the parallax error.

Figure 7:
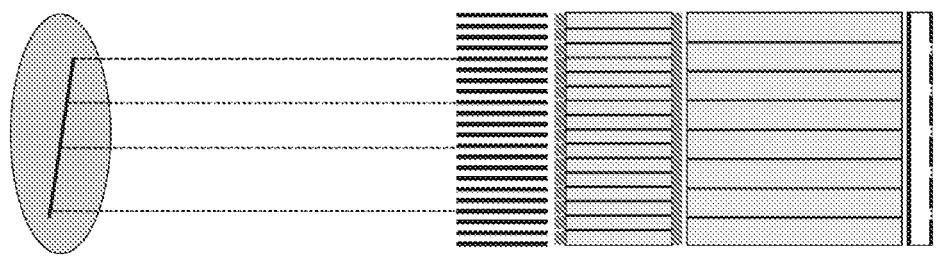

FIG. 7: Schematics of one possible embodiment of the PG-MON imager with a multi-hole collimator configuration. The image size equals the object size.

Figure 8:
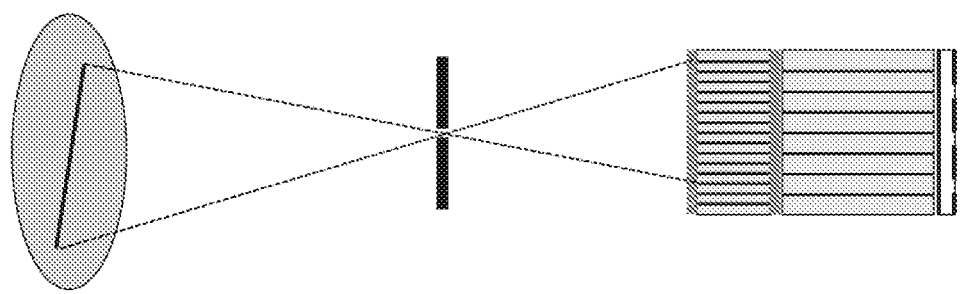

FIG. 8: Schematics of a possible embodiment of the PG-MON imager assembled as pinhole or knife edge camera. The image size can be adjusted moving the collimator position.

Figure 9:
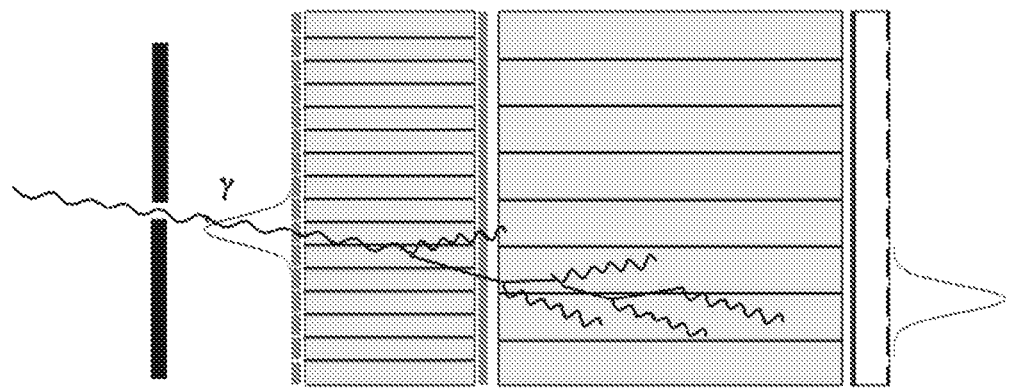

FIG. 9: Example on how, for gammas impinging the PG-MON at non-orthogonal angles, the positional information provided by the two detection layers can be combined to provide a coarse information of the incidence angle, thus permitting correction of the parallax error.

Figure 10:
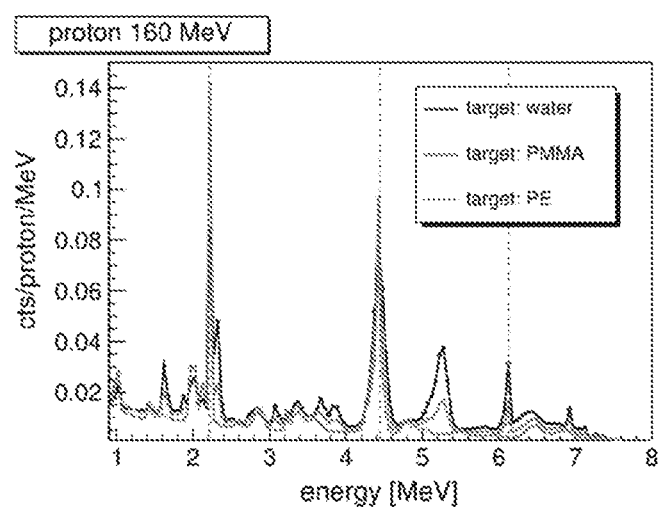

FIG. 10: Prompt gamma emission as a function of energy for different targets; 160 MeV proton beam (Krimmer 2018).

Figure 11:
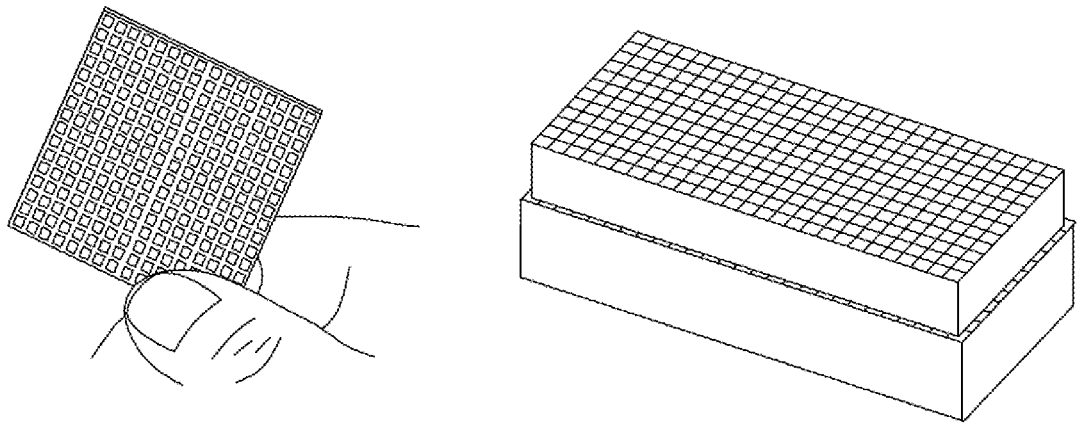

FIG. 11: Example of pixelated scintillator arrays (Saint Gobain)

Figure 12:
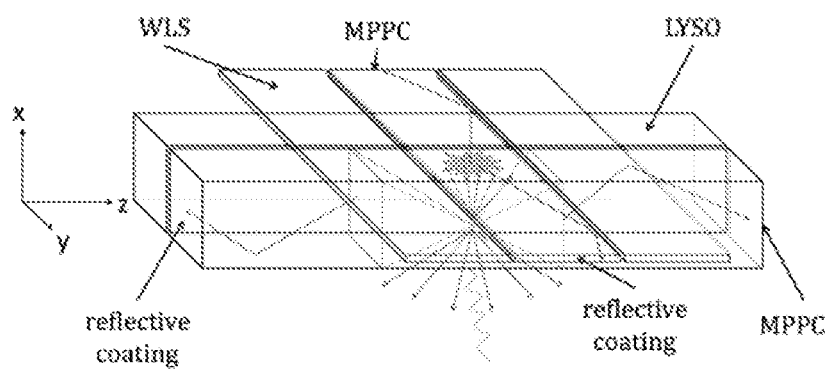

FIG. 12: Coupling of LYSO scintillator rods to SiPM (MPPC) with WLS bars (Beltrame 2011)

Figure 13:
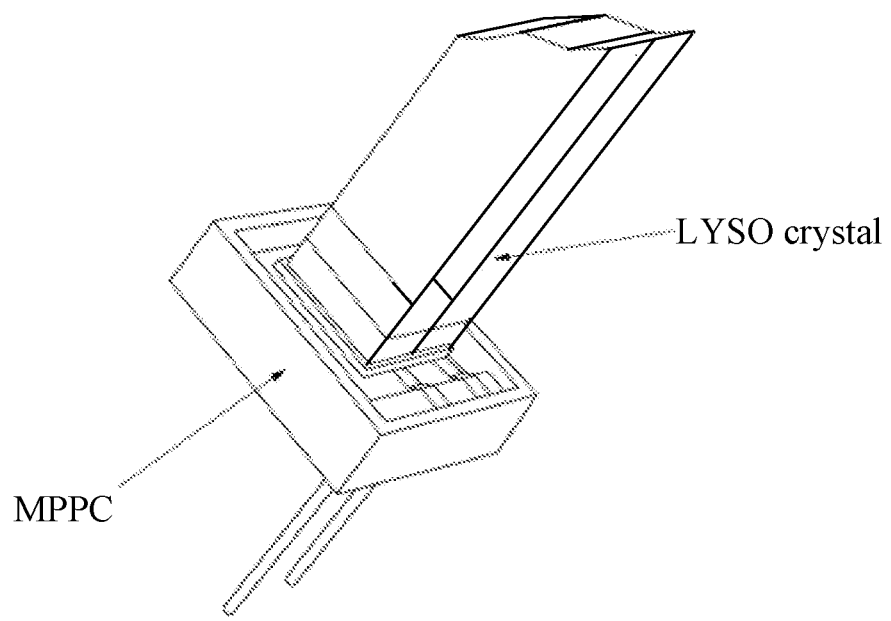

FIG. 13: Example of direct coupling of a LYSO scintillator rod to a SiPM (MPPC) (Beltrame 2011)

Figure 14:
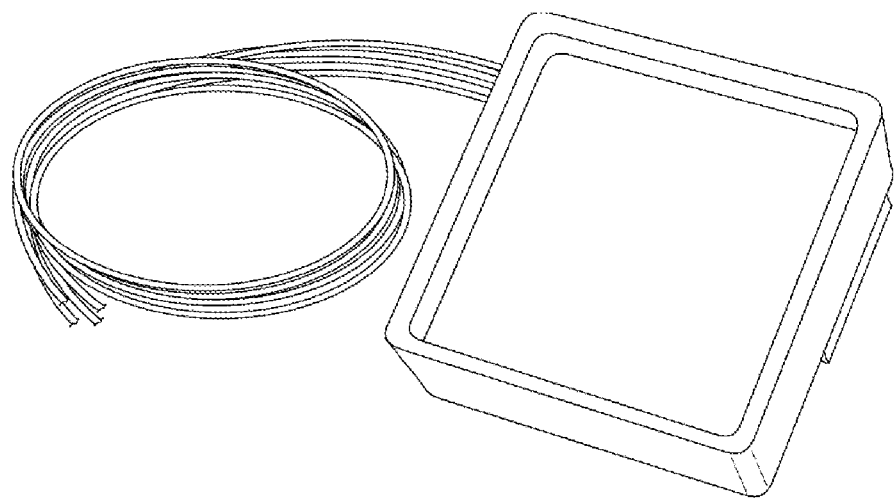

FIG. 14: Example of a 5×5 $cm^2$ multi-anode photomultiplier with 8×8 anodes 5.9×5.9 $mm^2$ each (Photonis XP85012 Planacon)

The processes leading to the conversion of photons and neutrons is shown schematically in FIG. 1. Two detection modules of high-density converters (commonly high atomic number inorganic scintillating crystals) are assembled in sequence. Gamma rays, in the energy range of interest for hadron therapy monitoring (a few to 10 MeV) interacting within the first block through electromagnetic interactions, Compton scattering or pair production, create a (small) electromagnetic shower composed of photons, electrons and positrons that propagates into the second block, until the full initial photon energy is completely absorbed. For neutrons, on the contrary, the interaction releases short-range nuclear debris mostly contained in the first or second detection module. A simple electronic selection of events with signals recorded in both detector within a pre-defined time window effectively selects the prompt gammas events over the neutron background.

The thickness of each layer, which ranges from a few mm to a few cm depending on the materials chosen, is essential for the correct functioning of the invention. Indeed, the first layer is thick enough to collect enough signal from the incoming neutron or photon but thin enough to enable the electromagnetic shower from the photon interaction to propagate to the second layer and to limit the natural lateral spread of the electromagnetic shower (first layer is most position-sensitive). The second layer (which can be formed of many crystals) should be thick enough to absorb practically all the energy from the electromagnetic shower. It should also be position sensitive, in case that the monitor is used to compute not only the position but also the incidence angle of the radiation.

The arrangement of the PG-MON instrument is shown schematically in FIG. 2. The functionally independent parts are shown separately, for a better understanding of the invention, but practically they are preferably assembled in a single device:

X1 and X2 are segmented assemblies of scintillating crystals, providing a first conversion layer (X1) and a second layer (X2) for the absorption of the electromagnetic shower generated by gamma rays converting in X1. Each layer is an assembly of closely packed and optically insulated thin scintillator rods, directing the scintillation light along their axis to suitable optical sensors to preserve localization. The two layers are optically shielded to provide independent signal outputs.

S1 and S2 are independent light sensors to detect the light flashes produced by the two blocks of scintillating materials; one or both are segmented in patterns that permit to perform localization of the scintillation flash in the plane of the detector, as shown in the detailed description.

The operating principle of the invention exploits the absorption of hard photons in stacks of segmented high-Z scintillators. While there is a wide choice of suitable scintillating crystals, with their high molecular weight and density LYSO (Cerium doped Lutetium based crystals) and lanthanum bromide ($LaBr_3$) are preferred choices as efficient converter for high-energy photons (Saint-Gobain Crystals Handbook). Two main processes contribute to the absorption in the few MeV region (FIG. 3, as an example for lanthanum bromide): Coherent Compton scattering (CC) and pair production in the nuclear field (PPN). The total gamma absorption coefficient is almost constant to around 0.04 $cm^2/g$, corresponding to an absorption length of about five cm in all the range of interesting photon energies. For 25 mm thick scintillators, the conversion efficiency is conveniently about 60% of the total PG flux.

Hard photons emitted by the beam-target interactions enter the detector and interact in the crystals; to limit the lateral spread of the scintillation signal, the converters are an assembly of closely packed, optically insulated individual crystals. After the first interaction, a cascade of events develops into a (few-photon) forward electro-magnetic shower, laterally spreading in the crystals until full absorption.

Localization of the interaction point can be performed with a wide choice of segmented photon detection devices: avalanche photodiodes, silicon photomultipliers, multi-anode vacuum photomultipliers, micro-channel plate sensors and more.

The most powerful readout structure, generally adopted for Positron Emission Tomography (PET) instrumentation, is a matrix of contiguous Silicon Photomultipliers (SiPM) with a pitch corresponding to the crystal lattice. For the S1 and S2 module of the PG-MON device, to reduce cost and complexity, the preferred embodiment of the invention is a two-dimensional projective readout of the crystals matrix realized coupling the scintillators to perpendicular sets of Wavelength Shifter strips (WLS) in contact with the opposite faces of the stack, and read-out by SiPM at the edges (FIG. 4). Analogue recording of the signals on all WLS strips, followed by an interpolation algorithm, provides localization accuracy better than the scintillators granularity, owing to the spread of the shower over several adjacent crystals.

The energy module S2 can be readout with a similar scheme but owing to the larger size of the crystals and the spread of the electromagnetic shower the use of a simpler and commercially available multi-anode photomultiplier on the end face could be more suitable. Previous work in the detectors development group of the TERA Foundation has demonstrated that with a center-of-gravity algorithm on the signals recorded on the MA-PM position accuracies around one mm can be achieved for a collimated $^{22}$Na 511 keV photon source (Solevi 2007).

To image a target, the PG-MON device can be mounted with a parallel hole collimator, a pinhole or a knife edge collimator (FIGS. 7 and 8). In the first scheme, the distance between patient and instrument is arbitrary, and the image size corresponds to the object size; in the second configuration instead, the image size can be enlarged or reduced varying the distances according to the needs.

Simpler and cheaper to manufacture, the pinhole and knife-edge collimators suffer from a fundamental limitation, as gammas can impinge the scintillator stack in a wide angular range, introducing parallax error dispersion as the depth in the crystal of the first interaction is unknown. The error can be coarsely corrected suitably combining the positional information provided by the two independent scintillator layers, as shown schematically in FIG. 9.

Advantageously, a neutron absorbing material may be placed as first element (closest to the patient) of the PG-MON. This element reduces the flux of neutrons impinging on the two active scintillator layers of the PG-MON. As an example, such a material could be composed of borated polyethylene at 30%. With a thickness of 20 cm, the neutron flux could thus be reduced by approximately a factor 3.

A further improvement on the neutron background rejection can be achieved by applying a selection in the total energy collected by the two layers, which enhances the signal from gammas and reduce the signal from neutrons. Such a selection window could be chosen to correspond to the known region of emission of prompt gammas, between 1 and 10 MeV.

An additional improvement of the neutron background rejection may be achieved by filtering the coincidence signals based on the angular correlation between the two layers, i.e. by selecting only the signals where there is a small position difference between the signal in the two layers. Indeed, for gammas, the generated shower propagates in the forward direction, whereas for neutrons, the generated shower propagates in wider directions. Therefore, for gammas, the coincidence signals is in the two layers at transverse positions close to each other, whereas for neutrons, the coincidence signals may also be located in very far apart transverse positions between the two layers.

REFERENCES AND RELATED ART

U. Amaldi, Use of linear ion accelerators for the treatment of atrial fibrillation and ion accelerator system there for, TERA Foundation, EP3036978 (2013).

J. Krimmer, D. Dauvergne, J. M. Letang, E. Testa, Prompt-gamma monitoring in hadrontherapy: A review, Nucl. Insr. and Meth. A 878(2017)58.

A. Braem et al, AX-PET: A novel PET detector concept with full 3D reconstruction, Nucl. Instr.and Meth. A610 (2009)192.

P. Solevi, Study of an in-beam PET system for CNAO, the National Centre for Oncological Hadrontherapy. PhD Thesis (Milano University, 2007).

D. Watts, Detectors for Quality Assurance in Hadrontherapy, Doctoral Thesis (Univ. Barcelona 2013)

C. Casella, M. Heller, C. Joram, T. Schneider, Nucl. Instr. and Meth,. A736(2014)161.

P. Beltrame et al, Construction and tests of demonstrator modules for a 3-D axial PET system for brain or small animal imaging, Nucl. Instr. and Meth. A636(2011)5226

I. Perali et al, Prompt gamma imaging of proton pencil beams at clinical dose rate, Phys. Med. Biol. 59(2014)5849.

Saint-Gobain Crystals Handbook (https://www.crystals.saint-gobain.com)

F. Sauli, Radiation Imaging with Gaseous Detectors, Nucl. Instr. And Meth. A878(2018)1.

German Patent Application DE 10 2013 102 920 A1.

The invention claimed is:

1. A prompt gamma monitor for patient dose monitoring in hadron therapy, said prompt gamma monitor comprising:
    a first detection module and a second detection module that are contiguous and independent and configured in a way as to let prompt gammas coming from a patient initially interact with the first detection module and generate an electromagnetic shower propagating to the second detection module, wherein the first detection module is thick enough to collect sufficient signal from an incoming neutron or photon but thin enough to enable the electromagnetic shower from interaction with the photon to propagate to the second detection module and to limit natural lateral spread of the electromagnetic shower and wherein the second detection module is thick enough to absorb a large fraction of the energy from said electromagnetic shower; and
    a signal detecting unit that is adapted to detect an electronic signal coincidence between said first detection module and said second detection module.

2. The prompt gamma monitor according to claim 1 wherein a thickness of the first module is between 5 mm and 100 mm.

3. The prompt gamma monitor according to claim 1 wherein a thickness of the second module is between 5 and 100 mm.

4. The prompt gamma monitor according to claim 1 wherein each of said first detecting module and said second detecting module is a LYSO or a lanthanum bromide scintillating crystal.

5. The prompt gamma monitor according to claim 1, wherein at least one of said first detecting module and said second detecting module is an assembly of closely packed and optically insulated thin scintillator rods that are adapted to direct the scintillation light along their axis to suitable optical sensors to preserve localization.

6. The prompt gamma monitor according to claim 1 wherein said first detecting module and said second detecting module are each optically shielded to provide independent signal outputs.

7. The prompt gamma monitor according to claim 1 comprising two light sensors located respectively in front and behind said first detecting module and said second detecting module.

8. The prompt gamma monitor according to claim 1 wherein the second detecting module enables a quantitative measurement of the energy released by the incoming radiation.

9. The prompt gamma monitor according to claim 1 wherein a two-dimensional projective readout of a crystals matrix is realized coupling scintillators to perpendicular sets of Wavelength Shifter strips (WLS) in contact with opposite faces of a stack, and read out by SiPM.

10. The prompt gamma monitor according to claim 9 wherein the read-out is made by SiPM at the edges.

11. The prompt gamma monitor according to claim 1 comprising a neutron absorbing material that is located in a way as to let prompt gammas coming from a patient first cross said neutron absorbing material before reaching the first detecting module.

12. The prompt gamma monitor according to claim 11, wherein said neutron absorbing material is composed of borated polyethylene at 30%.

13. The prompt gamma monitor according to claim 11 wherein said neutron absorbing material has a thickness of 20 cm.

14. A method of using a prompt gamma monitor, comprising:
providing a prompt gamma monitor including a first detection module and a second detection module that are contiguous and independent and configured in a way as to let prompt gammas coming from a patient initially interact with the first detection module and generate an electromagnetic shower propagating to the second detection module, wherein the first detection module is thick enough to collect sufficient signal from an incoming neutron or photon but thin enough to enable the electromagnetic shower from interaction with the photon to propagate to the second detection module and to limit natural lateral spread of the electromagnetic shower and wherein the second detection module is thick enough to absorb a large fraction of the energy from said electromagnetic shower, and a signal detecting unit adapted to detect an electronic signal coincidence between said first detection module and said second detection module: and
selecting a total energy collected by the first detection module and the second detection module.

15. The method according to claim 14 wherein the total energy selected in the step of selecting is between 1 and 10 MeV.

16. The method of claim 14, comprising filtering the electronic signal coincidence based on an angular correlation between the first detection module and the detection module.

17. A method for using a prompt gamma monitor, comprising:
providing a prompt gamma monitor including
a first detection module and a second detection module that are contiguous and independent and configured in a way as to let prompt gammas coming from a patient initially interact with the first detection module and generate an electromagnetic shower propagating to the second detection module, wherein the first detection module is thick enough to collect sufficient signal from an incoming neutron or photon but thin enough to enable the electromagnetic shower from interaction with the photon propagate to the second detection module and to limit natural lateral spread of the electromagnetic shower and wherein the second detection module is thick enough to absorb a large fraction of the energy from said electromagnetic shower, and
a signal detecting unit adapted to detect an electronic signal coincidence between said first detection module and said second detection module; and
filtering the electronic signal coincidence based on an angular correlation between the first detection module and the second detection module.

* * * * *